US006705987B2

(12) United States Patent
Anderson et al.

(10) Patent No.: US 6,705,987 B2
(45) Date of Patent: Mar. 16, 2004

(54) PENILE SEAL AND CONSTRICTION RING

(75) Inventors: David W. Anderson, Brooklyn Park, MN (US); Allen R. Pedersen, Bloomington, MN (US); Karl F. Biewald, Minneapolis, MN (US); Gerald W. Timm, Minneapolis, MN (US)

(73) Assignee: Endocare, Inc., Irvince, CA (US)

( * ) Notice: Subject to any disclaimer, the term of this patent is extended or adjusted under 35 U.S.C. 154(b) by 0 days.

(21) Appl. No.: 10/124,566

(22) Filed: Apr. 17, 2002

(65) Prior Publication Data

US 2003/0199734 A1 Oct. 23, 2003

(51) Int. Cl.$^7$ .................................................. A61F 5/41
(52) U.S. Cl. ......................................................... 600/38
(58) Field of Search ..................................... 600/38–41

(56) References Cited

U.S. PATENT DOCUMENTS

| 3,744,486 A | 7/1973 | Wilson |
| 3,820,533 A | 6/1974 | Jones |
| 4,175,554 A | 11/1979 | Gerow |
| 4,203,432 A | 5/1980 | Koch |
| 4,378,008 A | 3/1983 | Osbon |
| 4,539,980 A | 9/1985 | Chaney |
| 4,628,915 A | 12/1986 | Chaney |
| 4,641,638 A | 2/1987 | Perry |
| 4,690,135 A | 9/1987 | Gerow |
| 4,718,411 A | 1/1988 | Stewart |

(List continued on next page.)

FOREIGN PATENT DOCUMENTS

| CH | 347300 | 8/1960 |
| WO | 99-44550 | 9/1999 |

OTHER PUBLICATIONS

Urologly, Pp. 126–131, Feb. 1986 Nadig Et Al. noninvasive Device To Produce And Maintain An Erection–Like State.
Urologic Clinics Of North America V. 15, Pp. 123–128, Feb. 1988, Witherington, Suction Device Therapy In The Management Of Erectile Impotence.
British Medical Journal V.296, Pp. 161–162, Jan. 1988, Wiles, Successful Non–Invasive Management Of Erectile Impotence In Diabetic Men.
Journal of Urology V. 140. Pp. 975–979. Nov. 1988, Marmar Et Al., The Use Of A Vacuum Constriction Device To Augment A Partial Erection.
Journal. of Urology V.141, Pp. 320–322, 1989, Witherington, Vacuum Contriction Device For Management Of Erectile Impotence.

(List continued on next page.)

Primary Examiner—Samuel G. Gilbert
(74) Attorney, Agent, or Firm—Merchant & Gould P.C.

(57) ABSTRACT

The present invention relates generally to a vacuum erection device, and more particularly with a combined vacuum seal and penile constriction ring used in conjunction with the vacuum erection device. One embodiment of the invention is a penile seal and constriction ring device that includes a webbing member having an outer circumference, a retaining ring defining an outer diameter of the device, and a sealing ring disposed between the retaining ring and the webbing member. The sealing ring is radially spaced from the retaining ring and includes an exterior surface. The exterior surface of the sealing ring is capable of forming a seal with a second surface independent from the exterior surface of the sealing ring. The device also includes an aperture with sidewalls formed in the webbing member. In a further embodiment, the device is capable of attaching to a vacuum cylinder. In this embodiment, the exterior surface of the sealing ring engages an interior surface of the vacuum cylinder to form a seal. Also, the sidewalls of the aperture are capable of forming a seal around an exterior of a penis and constrict vessels of the penis.

14 Claims, 4 Drawing Sheets

U.S. PATENT DOCUMENTS

| | | |
|---|---|---|
| 4,741,329 A | 5/1988 | Marcune |
| 4,753,227 A | 6/1988 | Yanuck |
| 4,856,498 A | 8/1989 | Osbon |
| 4,856,499 A | 8/1989 | Kelly |
| 4,960,113 A | 10/1990 | Seeberg-Elverfeldt |
| 4,995,381 A | 2/1991 | Marmar et al. |
| 5,020,522 A | 6/1991 | Stewart |
| 5,095,895 A | 3/1992 | Walsh |
| 5,115,800 A | 5/1992 | Matejevic et al. |
| 5,125,890 A | 6/1992 | Merrill et al. |
| 5,195,943 A | 3/1993 | Chaney |
| 5,213,563 A | 5/1993 | Cox |
| 5,221,251 A | 6/1993 | Edminster |
| 5,234,402 A | 8/1993 | Osbon |
| 5,243,968 A | 9/1993 | Byun |
| 5,244,453 A | 9/1993 | Osbon et al. |
| 5,306,227 A | 4/1994 | Osbon et al. |
| 5,338,288 A | 8/1994 | Finkle |
| 5,344,389 A | 9/1994 | Walsdorf et al. |
| 5,421,324 A | 6/1995 | Kelly |
| 5,421,808 A | 6/1995 | Osbon et al. |
| 5,707,341 A | 1/1998 | Mathewuse |
| 5,951,460 A * | 9/1999 | Vollrath ..................... 600/38 |
| 6,036,635 A | 3/2000 | Altshuler |
| 6,306,080 B1 | 10/2001 | Mitchell et al. |

OTHER PUBLICATIONS

Journal. Of Urology V.142, Pp. 1087–1089, 1989, Diederichs Et Al., The Effect of Subatmospheric Pressure On The Simian Penis.

Journal. Of Urology V. 142, P 1086, Dec. 1989, Sharlip, Vacuum–Induced Erection.

Journal Of Urology V. 144, Pp. 79–82, Dec. 1990, Turner Et Al., Vacuum Devices To Treat Erectile Disfunction.

Diabetic Medicine V.8 Pp. 964–967, Dec. 1991, Price Et Al, The Management Of Impotence In Diabetic Men By Vacuum Tumescence Therapy.

Journal. Of Urology V.149, Pp. 1285–1287, May 1993 Meinhardt Et Al., The Negative Pressure Device For Erectile Disorders: When Does It Fail?.

British Journal Of Ur., Dec. 1994, Vrijhof Et Al., Vacuum Constriction Devices In Erectile Disfunction: Acceptance And Effectiveness In Patients With Impotence Of Organic And Mixed Aetiology.

* cited by examiner

PENILE SEAL AND CONSTRICTION RING

BACKGROUND OF THE INVENTION

1. Field of Invention

The invention relates to vacuum constriction devices, and more particularly to a combined penile seal and constriction ring for use with a vacuum constriction device.

2. Related Art

In recent years, non-invasive devices have been designed and used for the external management of erectile dysfunction, in part because of the cost and risk involved with surgical implantation of penile prostheses. External constriction devices commonly contract around the base of the flaccid penis and prevent the outflow of blood once the penis has risen into an erect state. Several different styles of constriction devices exist that obtain this same result.

The first category of constriction devices is a constricting ring that may be used alone or in combination with an external erection device. The constriction ring is placed on an erected penis to impede the flow of blood to maintain an erect state. These devices are typically made of an elastomeric material such as rubber. A constriction ring generally consists of O-rings with shaped handles attached to the ring to assist in applying and removing the ring. By grasping the handles, the central O-ring is stretched and placed over the base of the penis where it constricts the retraction vessels to prevent outflow of blood.

When used alone, the constriction ring is placed around the base of a flaccid or semi-flaccid penis, constricting the blood vessels of the penis before it is brought to an erect state. The penis is then manipulated to encourage blood flow into the penis and the constriction ring prevents the outflow of blood to enable the user to achieve and maintain an erection.

A second category of constriction devices is designed for use with suction or vacuum erection devices. Vacuum erection devices typically include an elongated vacuum cylinder, sometimes with tapered walls, that is usually made of a clear polymeric material with a length and diameter sufficiently large to accommodate either a flaccid or an erect penis. At a first end of the cylinder, a vacuum device is secured to the cylinder to remove air either with a manually operated or electronic vacuum pump. At a second end of the cylinder, a constriction device such as a constriction ring or sleeve is secured to or slipped over the end of the cylinder. Once the constriction ring or the like is placed around the second end of the cylinder, the cylinder is positioned over the flaccid penis and pressed against the user's abdomen. While pressing the cylinder firmly against the user's abdomen around the base of the penis, the vacuum pump is operated to evacuate air from the cylinder. The resulting reduction of air pressure around the penis causes blood to engorge the penis, bringing it to an erect state. Once erection is achieved, the constriction ring is removed from the second end of the cylinder and contracts around the base of the erect penis. Placement of the ring around the erect penis significantly restricts the flow of blood back out of the penis, thereby maintaining the penis in an erect state until such time as the ring is removed.

Several problems have been identified using the above-mentioned systems. First, the vacuum cylinder used to mount the constriction device and create an airtight seal between an open end of the cylinder and the user's abdomen is often ineffective for creating an airtight seal. Furthermore, creating a vacuum tight seal against the abdomen often permits abdominal or scrotal tissue and pubic hair to be painfully pulled into the vacuum chamber. Second, constriction devices are often used by older men who may have arthritis, muscle weakness, and vascular or nervous degeneration that inhibits their ability to stretch the constriction ring over the vacuum chamber or penis and provide the necessary force required to maintain a tight vacuum seal between the cylinder and the abdomen of the user. A third disadvantage of known constriction devices is that the constriction devices are difficult to mount to an exterior of the vacuum cylinder. Constriction ring stretchers and loaders are sometime provided with vacuum erection devices and constriction rings to expand and load the constriction ring to the cylinder. These stretchers and loaders, however, are often complicated to use, often break the constriction rings, and are expensive to manufacture and purchase. Lastly, the constriction rings typically snap off the vacuum cylinder onto the penis with great force, like a rubber band, which often surprises and hurts the user.

A combination constriction ring and abdominal sealing pad has been described by Wallsdorf, U.S. Pat. No. 5,344, 389. This device is expanded with a ring stretcher, placed over the penis, and released to constrict the penis. A vacuum chamber is then placed around the penis, contacting the sealing pad, and a vacuum is generated between the abdominal sealing pad and an end surface of the vacuum cylinder. The vacuum condition causes blood to be drawn past the ring and into the penis. The abdominal sealing pad prevents abdominal or scrotal tissue and pubic hair from being pulled into the vacuum chamber. However, this device suffers from some of the disadvantages described above for known vacuum systems.

A vacuum seal on the penis, rather than the abdomen, has been described by Altshuler, U.S. Pat. No. 6,036,635. Altshuler describes a sleeve that is stretched over the opening of the vacuum chamber to create a vacuum seal between the sleeve and the outer surface of the vacuum cylinder, and between the sleeve and the penis. The system of Altshuler also includes a ribbon-shaped constriction device that is wound over itself to form a cylindrical ring that is secured to the cylinder on top of the sleeve with a belt. This device minimizes discomfort due to abdominal tissue entrapment, but maintains several disadvantages. For example, this penile seal limits the achievable vacuum pressure and the quality of the erection because both a penile seal and a ribbon shaped constriction device are used. Further, stretching the seal over the vacuum cylinder may be difficult. In addition, the penile constriction ring required to hold the blood within the penis after engorgement and the sleeve are separate members, thus increasing the cost and complexity of the system. Also, removal of the separate constriction ring from the vacuum cylinder is intended to simultaneously remove the penile seal from the cylinder and break the vacuum seal. Placement of the constriction ring is therefore technique-dependent and does not provide consistent results. Lastly, the penile seal must be removed before sexual intercourse.

A combination penile seal and constriction ring is disclosed by Bonthuys, WO99/44550. This device provides a penile seal and sealing ring that is mountable on a vacuum cylinder. The device is mounted to an end of the vacuum cylinder, the penis is placed against a ring opening of the device, and the penis is drawn into the vacuum cylinder under vacuum pressure. Once seated at the base of the penis, the ring constricts and prevents venous outflow from the penis while blood is drawn into the penis under vacuum pressure. The ring is then removed from the vacuum cylinder and remains on the penis until removed by the user. To remove the ring, the opening of the ring is manually stretched to allow removal of the ring thereby permitting blood to exit the penis. The sealing ring includes a ring-shaped portion with an inward facing surface or wall that engages the outside and end surfaces of the cylinder to form a vacuum seal. The diameter of the inward facing surface of the ring-shaped portion is slightly smaller than the outside diameter of the vacuum cylinder so that the device is sealingly engaged to the outside surface of the vacuum cylinder.

SUMMARY OF THE INVENTION

The present invention generally relates to penile constriction rings for treatment of erectile dysfunction. One embodiment of the invention is a penile seal and constriction ring device with a webbing member that acts as a base for the device and has an outer circumference. The device includes a sealing ring portion that is spaced radially inward from the webbing member outer circumference. The sealing ring portion has a radially outward facing surface that is capable of forming a seal with a second surface. The device further includes an aperture formed in the webbing member that forms a penile seal and constricts the penis.

The invention particularly relates to a penile seal and constriction ring device for a vacuum constriction device. When used with a vacuum constriction device, the sealing ring portion of the penile seal and constriction ring device forms a seal with an inner surface of a vacuum cylinder portion of the vacuum constriction device. The aperture of the penile seal and constriction device includes sidewalls that form a seal around the penis and constrict vessels of the penis. The device may also include a retaining ring portion of the webbing member that is formed at the webbing member outer circumference. The retaining ring portion engages an outer surface of the vacuum cylinder and includes features, such as channels, formed in the retaining member that prohibit a seal being formed between an outside or end surface of the vacuum cylinder and the device.

According to a method of the invention, the penile seal and constriction ring device is placed on a first end of a vacuum cylinder and a seal is formed between the radially outwardly facing surface of the sealing ring and the inner surface of the vacuum cylinder.

A system for treatment of erectile dysfunction, according to the invention, includes a vacuum cylinder, a vacuum pump secured to one end of the vacuum cylinder, and a penile seal and constriction ring device removably mounted to another end of the vacuum cylinder. The penile seal and constriction ring device of the system includes a webbing member with an outer circumference, a sealing ring portion radially spaced inwardly from the webbing member outer circumference and having a radially outwardly facing surface that is capable of forming a seal with the inner surface of the vacuum cylinder, and an aperture formed in the webbing member.

The above summary of the present invention is not intended to describe each disclosed embodiment or every implementation of the present invention. The figures and the detailed description that follows more particularly exemplify these embodiments.

BRIEF DESCRIPTION OF THE DRAWINGS

The invention may be more completely understood in consideration of the following detailed description of various embodiments of the invention in connection with the accompanying drawings, wherein like numerals represent like parts throughout several views, in which.

While the invention is amenable to various modifications and alternative forms, the specifics thereof have been shown by way of example in the drawings and will be described in detail. It should be understood, however, that the intention is not to limit the invention to the particular embodiments described. On the contrary, the intention is to cover all modifications, equivalents, and alternatives falling within the scope and spirit of the invention.

DETAILED DESCRIPTION OF THE PREFERRED EMBODIMENT

The present invention is believed to be applicable to vacuum erection devices and their components. In particular, the present invention is directed to a combined penile seal and constriction ring device used in conjunction with a vacuum erection system that creates a seal between a sealing ring of the device and an inner surface of a vacuum cylinder of the system. While the present invention may not be so limited, an appreciation of various aspects of the invention will be gained through a discussion of the examples provided below.

The penile seal and constriction ring device of the present invention addresses many of the disadvantages of known penile seals and penile constriction rings and their combinations, particularly those used with a vacuum erection device. The present invention accomplishes these objectives by providing a device that creates a seal with both a vacuum cylinder and a penis to which the device is secured without requiring extensive stretching or deformation of the device to mount it to either the vacuum cylinder or the penis.

The present invention is directed to a combined penile seal and constriction ring device that includes a webbing member having an outer circumference, a sealing ring portion of the webbing member, and an aperture formed in the webbing member. The sealing ring portion is radially spaced inwardly from the webbing member outer circumference and has a radially outwardly facing surface that is capable of forming a seal with a second surface. The aperture formed in the webbing member forms a seal around a penis and constrict vessels of the penis. In a vacuum constriction system, the radially outwardly facing surface of the sealing ring portion forms a seal with an inner surface of a vacuum cylinder portion of the vacuum constriction system.

One advantage of the penile seal and constriction ring device of the present invention is the simplified attachment of the device to a user's penis and to a vacuum cylinder of a vacuum constriction system, while also ensuring a vacuum seal between the device, the vacuum cylinder and the user's penis. The present invention may further include features to enable a user of the device to easily remove the device after use.

Referring now to FIGS. 1–4, one embodiment of a penile seal and constriction ring device 10 of the present invention is shown. One application of device 10 is for use with a vacuum erection system 100 (See FIG. 3) that treats erectile dysfunction. System 100 includes a vacuum cylinder 102, a vacuum pump 104 secured to one end of the vacuum cylinder, and the penile seal and constriction ring device 10 removably mounted to another end of cylinder 102 (See FIG. 4). Vacuum cylinder 102 includes a first end 106 to which device 10 is secured, a second end 108 to which vacuum pump 104 is secured, an inner surface 110, an outer surface 112, and an end surface 114 at first end 106.

In the embodiment of FIGS. 1–4, webbing member 12 includes two substantially planar first and second major surfaces 20 and 22 that generally oppose each other. An outer circumference of webbing member 12 is defined by retaining ring 16. The sealing ring portion 14 of the webbing member is formed from first major surface 20 of the webbing member at a location radially inwardly spaced from the webbing member outer circumference. The sealing ring portion extends generally perpendicular from the webbing member and includes a radially outwardly facing surface 24 and a radially inwardly facing surface 26. The radially outwardly facing surface 24 and the radially inwardly facing surface 26 of sealing ring portion 14 face perpendicular to first major surface 20. In other embodiments, outwardly facing surface 24 and inwardly facing surface 26 may face at an angle other than perpendicular from surface 20, so long as surface 24 is able to form a seal with inner surface 110 of vacuum cylinder 102.

Sealing ring portion 14 also has an outer diameter that may be slightly greater than an inner diameter of vacuum cylinder 102 that is defined by inner surface 110. Accordingly, an interference fit may be provided between surface 24 and surface 110 to form a vacuum tight seal even prior to a vacuum condition being formed within vacuum cylinder 102. This interference fit between surfaces 24 and 110 also provides an attachment mechanism for removably securing device 10 to vacuum cylinder 102. According to this embodiment, mounting device 10 to cylinder 102 using an interference fit on inner surface 110 of the cylinder does not require stretching or deforming device 10 by hand or with additional tools.

In other embodiments, the inner diameter of cylinder 102 and the outer diameter of sealing ring portion 14 are substantially the same diameter such that an interference fit does not exist between sealing ring portion 14 and surface 110 of vacuum cylinder 102. Accordingly, a vacuum seal is formed between surface 24 of sealing ring portion 14 and inner surface 110 after a vacuum pressure is applied within cylinder 102.

Webbing member 12 also includes a retaining ring portion 16 that extends in a generally perpendicular direction from major surface 20. Retaining ring portion 16 may, for example, extend from either major surface 20 or from an outer circumference surface (not shown) of webbing member 12. In the perpendicular extending position illustrated in FIGS. 1 and 4, retaining ring portion 16 engages outer surface 112 and end surface 114 of vacuum cylinder 102.

Figure 1:
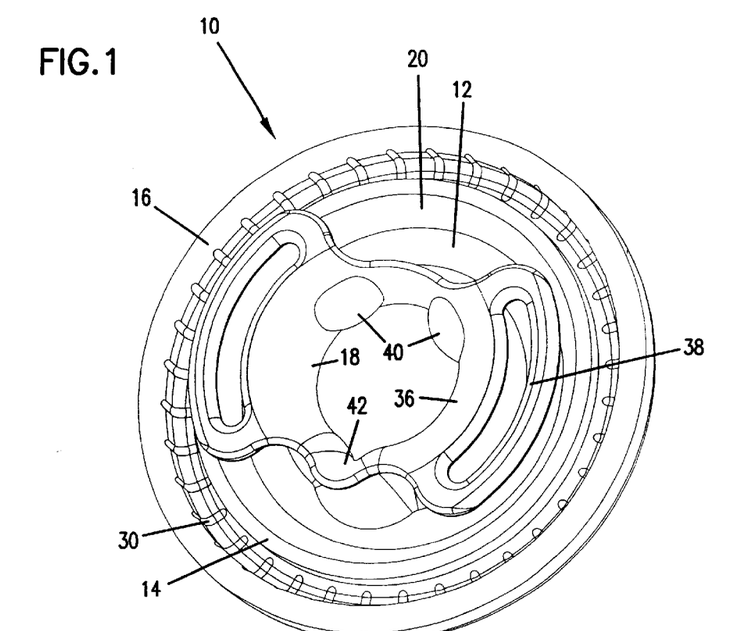
FIG. 1 is a front perspective view of a penile seal and constriction ring device, according to the invention.
Figure 2:
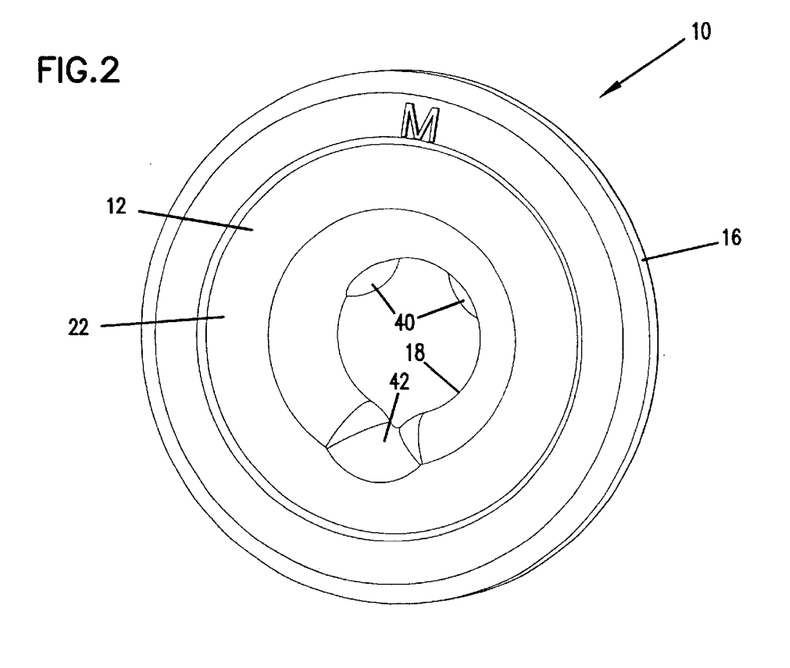
FIG. 2 is a rear perspective view of the penile seal and constriction ring device of FIG. 1.
Figure 3:
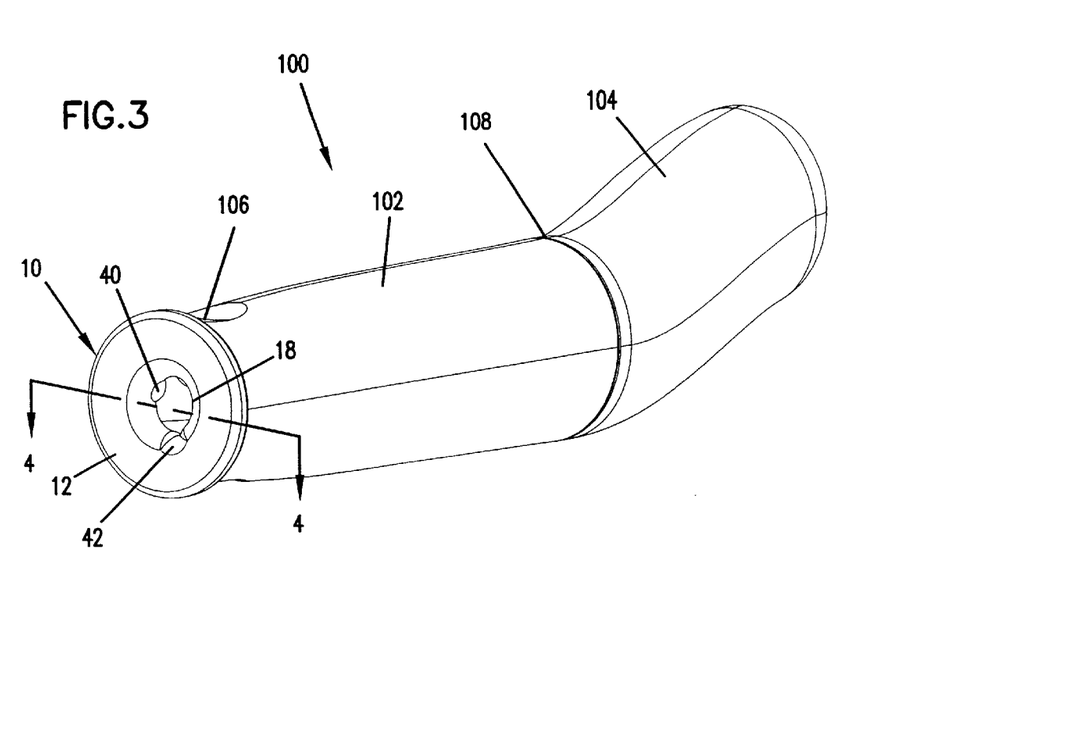
FIG. 3 is a perspective view of the penile seal and constriction ring device of FIG. 1 mounted to an end of a vacuum cylinder.
Figure 4:
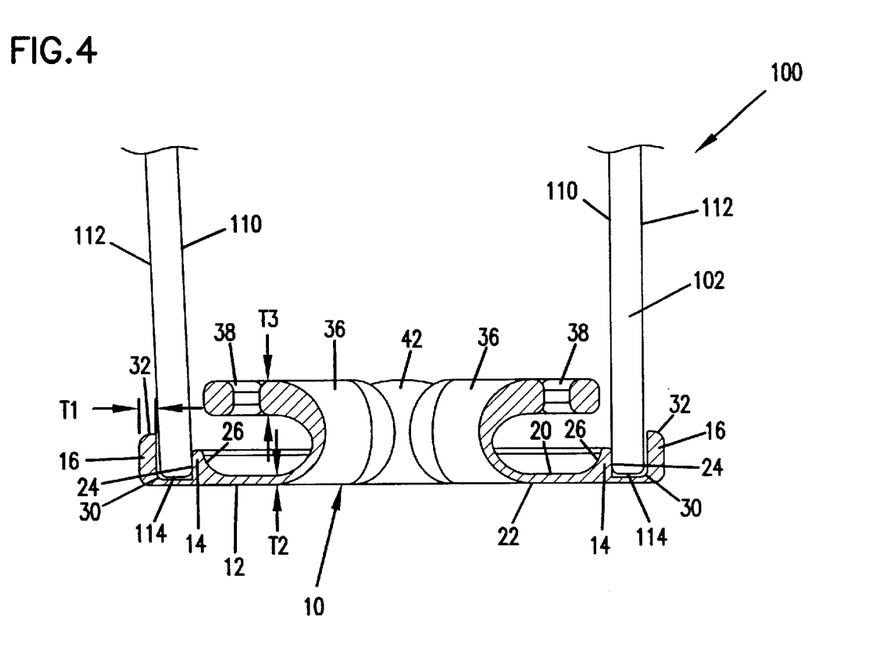
FIG. 4 is a partial cross-sectional view of the penile seal and constriction ring device and vacuum cylinder of FIG. 3.

Retaining ring portion 16 and webbing member 12 include channels 30 that extend radially from a base portion of outwardly facing surface 24 to an end 32 of retaining member 16. Channels 30 prohibit a seal being formed between retaining ring 16 and webbing member 12 and the exterior surface 112 and end surface 114 of vacuum cylinder 102. Channels 30 are radially spaced around device 10 to prohibit a seal being formed between the vacuum cylinder 102 and device 10 except at the interface between outwardly facing surface 24 of device 10 and the inner surface 110 of vacuum cylinder 102. Channels 30 may also improve the pliability of retaining ring portion 16 and that portion of webbing member 12 that extends radially outwardly from the location of sealing ring portion 14 on webbing member 12. Pliability may be advantageous for a penile seal and constriction ring device because the device typically engages a portion of the user's abdomen when the device is used with vacuum erection system 100. Pliability of device 10, particularly of retaining ring portion 16, may improve comfort while maintaining the required functional stiffness of the retaining ring portion and device 10 as a whole.

In other embodiments, channels 30 may be significantly reduced in number compared to the number shown in the embodiment of FIG. 1. In such an alternative embodiment, the pliability of retaining ring portion 16 and webbing member 12 may not be significantly changed by reducing the number of channels, while prohibiting a seal the same as the embodiment of FIG. 1.

As shown in the cross-sectional view of FIG. 4, retaining ring portion 16 has a thickness T1 that is greater than a thickness T2 of webbing member 12 between first and second major surfaces 20 and 22. The greater thickness of T1 relative to T2 enhances the ability of retaining ring portion 32 to retain device 10 at first end 106 of vacuum cylinder 102 so that the device is not pulled into the interior of the cylinder when a vacuum pressure is applied.

In a further embodiment, channels 30 may be ridges or other shaped protrusions rather than channel features. The ridges would produce a similar effect as channels 30 to prohibit a seal being formed between retaining ring portion 16 and webbing member 12 and the exterior and end surfaces 112 and 114 of vacuum cylinder 102. According to this embodiment, the thickness T1 of retaining ring portion 16 may be similar to or smaller than the thickness T2 of webbing member 12 and the ridges function to stiffen device 10. The size, shape and number of ridges that replace channels 30 may vary depending on the design requirements of a given penile seal and constriction ring device and the materials being used for the device.

Aperture 18 formed in webbing member 12 includes sidewalls 36, handles 38, dorsal vein constriction features 40, and a urethral notch 42. Aperture 18 is generally circular in shape and may have a diameter substantially equal to the exterior diameter of a flaccid penis. The thickness of sidewalls 36 may vary (see FIG. 4) between the thickness T2 of webbing member 12 and a thickness T3 near the attachment of handles 38 to the sidewalls. The properties and thickness of the material used for sidewalls 36 and webbing member 12 allow aperture 18 to increase in size by either pulling radially outwardly on handles 38 or by radial forces from growth of a penis to which device 10 is secured.

Dorsal vein constriction features 40 are positioned around aperture 18 so that they are aligned with dorsal veins of the penis. Thus, as the penis is engorged with blood through arteries feeding the penis, the dorsal vein constriction features 40 restrict blood from exiting the penis. In other embodiments, one or more vein constriction features 40 may be utilized.

Urethral notch 42 is positioned around aperture 18 on sidewall 36, possibly at an opposite side of opening 18 from dorsal vein constriction features 40. Urethral notch 42 is intended to be aligned with the urethra of the penis when device 10 is properly mounted to the penis to allow fluid flow through the urethra despite the constriction forces of sidewalls 36 around the penis.

In other embodiments, dorsal vein constriction features 40 and urethral notch 42 may be removed from aperture 18 and sidewalls 36. In such an embodiment, device 10 may still provide the required constriction of penile vessels necessary to maintain a penile erection, but may inhibit the outflow of fluid from the urethra.

Figure 5:
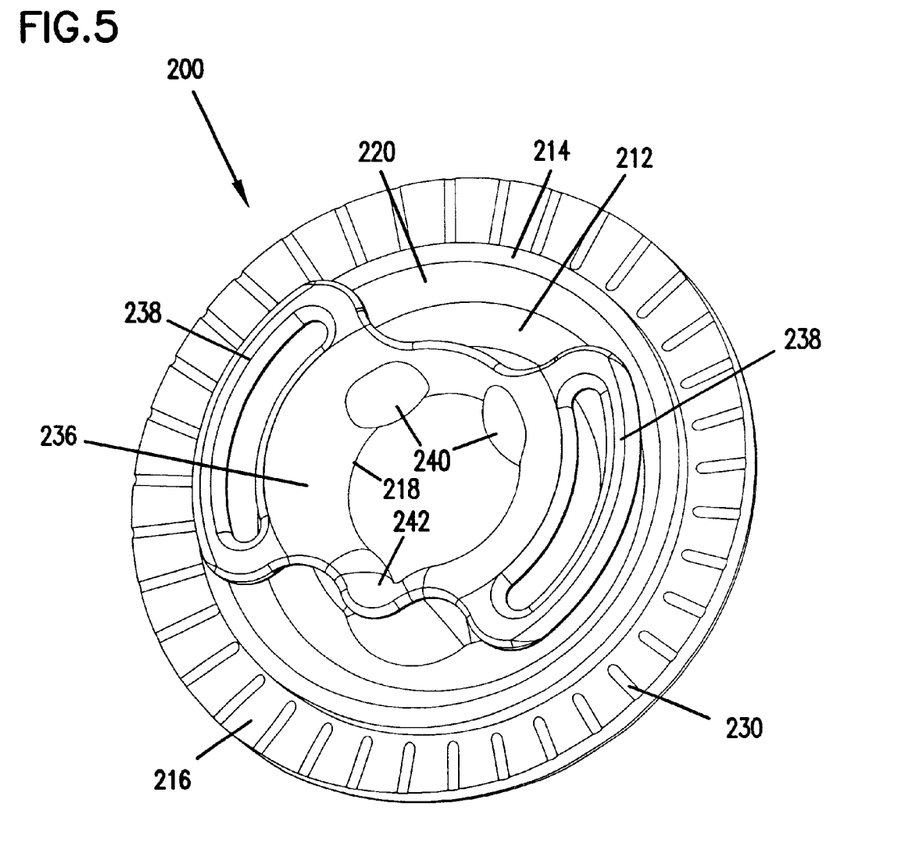
FIG. 5 is a front perspective view of an alternative embodiment of a penile seal and constriction ring device, according to the invention.
Figure 6:
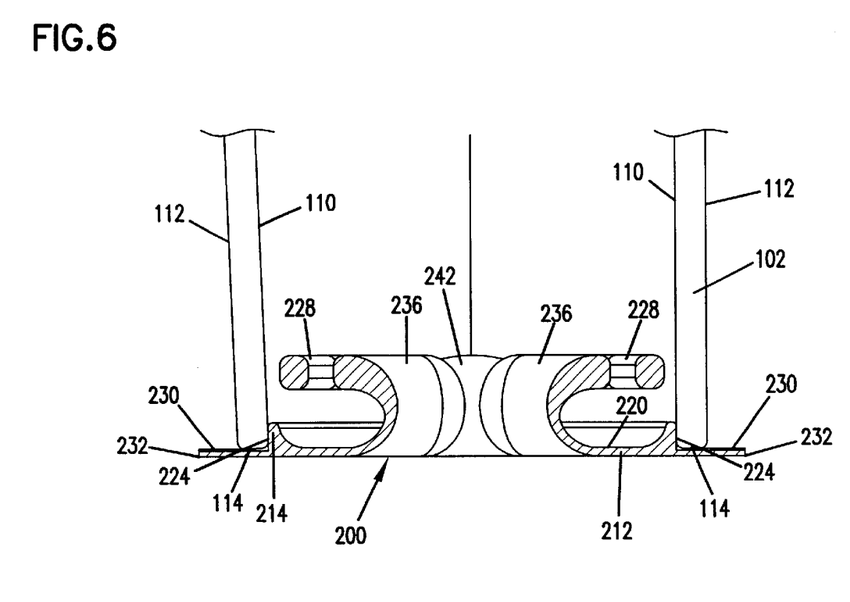
FIG. 6 is a partial cross-sectional view of the penile seal and constriction ring device of FIG. 5.

The alternative embodiment of FIGS. 5 and 6 illustrate a device 200 with the same or similar features as device 10, with the exception of retaining ring portion 16 being removed. Device 200 includes a retaining portion 216, a webbing member 212 and a sealing ring portion 214. The retaining portion 216 may be substantially flat and parallel with webbing member 212, and may be characterized as an extension of webbing member 212 that extends radially outward from the sealing ring portion 214 and defines an outer circumference of the webbing member. The retaining portion 216 also includes channels 230 that extend from outwardly facing surface 224 to an end surface 232 of the device. Channels 230 may be replaced with ridges that stiffen retaining portion 216 and, like channels 230, prohibit a seal being formed between retaining portion 216 and the outer and end surfaces 112 and 114 of a vacuum cylinder 102 to which the device 10 is secured.

Device 200 also includes a first major surface 220, an aperture 218 with sidewalls 236, handles 238, dorsal vein constriction features 240, and a urethral notch 242. Device 200 further includes an outwardly facing surface 224 of sealing ring portion 214 that forms a seal between device 10 and an inner surface 110 of vacuum cylinder 102.

Figure 7:
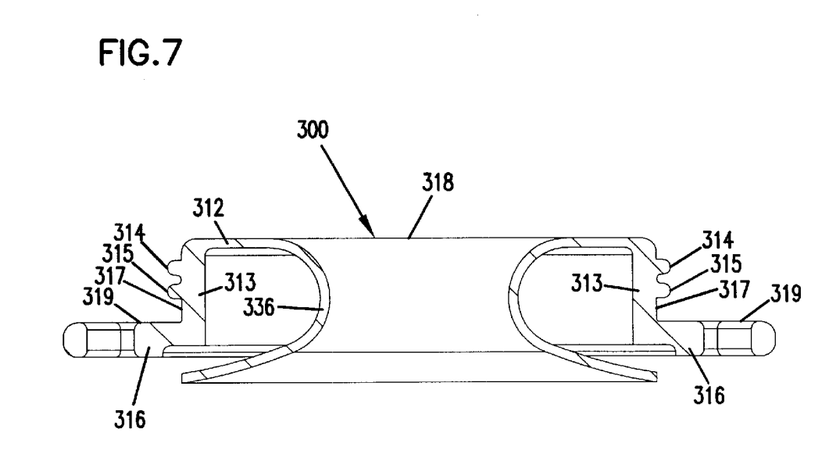
FIG. 7 is a cross-sectional side view of an alternative embodiment of a penile seal and constriction ring device, according to the invention.

An example of a penile seal and constriction ring device 300 having alternative features to devices 10 and 200 is shown in FIG. 7. Device 300 includes a webbing member 312, a sidewall portion 313, upper and lower sealing ring portions 314 and 315, a retaining portion 316, and an aperture 318 having aperture sidewalls 336. The aperture sidewalls 336 may extend axially from webbing 312 either into or away from vacuum cylinder 102. The sidewall portion 313 extends perpendicular from webbing 312 and may extend in the same direction aperture sidewalls 336 extend from webbing 312.

The upper and lower sealing rings 314 and 315 are positioned on an outwardly facing surface 317 of sidewall portion 313. An outer diameter of the sealing rings 314 and 315 are substantially the same or slightly larger than an inner diameter of a vacuum cylinder so that a vacuum seal may be formed between device 300 and the vacuum cylinder when device 300 is secured to an end of the vacuum cylinder.

The retaining portion 316 extends generally radially outwardly from sidewall portion 313 in a direction substantially parallel to webbing 312. An inner surface 319 of retaining portion 316 engages an end surface of a vacuum cylinder and is provided with sufficient rigidity to prohibit device 300 from being sucked into the vacuum cylinder when a vacuum pressure is applied inside the cylinder. In other embodiments, retaining portion 316 may be shaped similar to retaining ring 16 shown in FIGS. 1–4 so that it engages both an end surface and an outer surface of the vacuum cylinder. Channels or ridges (not clearly shown) are formed on inner surface 319 in all embodiments to prohibit a vacuum seal from being formed between device 300 and an end or exterior surface of the vacuum cylinder.

In other embodiments, device 300 may include handles, dorsal vein constriction features and a urethral notch on aperture sidewalls 336. Also, there may be only one sealing ring, or two or more sealing rings extending from sidewall 313, depending on a given configuration of device 300.

According to a method of the invention, the device is placed on the first end of the vacuum cylinder. The outer diameter of the sealing ring portion is substantially equal to or slightly larger than the inner diameter of the vacuum cylinder defined by its inner surfaces. Thus, a seal is maintained between the radially outwardly facing surface of the sealing ring portion and the inner surface at least at the time a vacuum pressure is applied on the interior of the cylinder. Further, the device, after being placed on the first end of the vacuum cylinder, is placed against the end of a flaccid penis with the end of the penis against the aperture. The vacuum pump, mounted to the vacuum cylinder second end, then applies a vacuum pressure to the interior of the vacuum cylinder. The vacuum pressure pulls the flaccid penis into the vacuum cylinder to a position where the second major surface of the webbing member engages abdominal tissue of the user at the base of the penis. The vacuum pressure draws blood into the penis, causing an erection. At the desired time, the user then removes the device from the first end of the cylinder, breaking the vacuum seal, and positioning the constriction ring at the base of the penis to prohibit outflow of blood from the erect penis into the user's body. When the user is ready to remove the device, the user may pull radially outwardly on the handles to enlarge the aperture in order to remove the device.

According to an alternative method of the invention, the aperture is expanded by pulling radially outwardly on the handles of the device, and the device is drawn onto a flaccid penis to a desire position on the penis. The vacuum cylinder is positioned over the flaccid penis and engages the device to form a seal between the inner surface of the vacuum cylinder and the radially outwardly facing surface of the sealing ring portion. The vacuum pump is then secured to an opposite end of the vacuum cylinder and a vacuum pressure is applied to the interior of the vacuum cylinder.

In further embodiments, the thickness T1 of the webbing member may vary between the aperture and the outer circumference of the webbing member. Different webbing member thicknesses may be advantageous for allowing stretching of the webbing member near its center to account for the change in outer diameter between a flaccid penis and an erect penis, while providing sufficient structural rigidity near the outer circumference of the device to prevent the device from being sucked into a vacuum cylinder when using the device.

Typically, the device is molded from a single material as a single piece by, for example, injection molding of the device. Such an integrally formed member improves manufacturability and ensures that the different features of the device, such as the sidewalls, handles, sealing ring portion, and retaining ring portion are properly secured to the webbing member and are less likely to be removed during use of the device. However, in other embodiments, the device may be made of several different materials, wherein each material is used for a specific feature and the device is formed as a single piece. In such an example, the retaining portion may be made of a material that is more rigid than the material of the sidewalls of the aperture, which are desirable to be very elastic. In a preferred embodiment, however, the device is injection molded of an elastic, polymeric material, wherein the entire unit is monolithic.

When creating a seal between the device and a flaccid penis, it is often advantageous to apply a coating of lubricant, such as KY Jelly® or a similar product, around the inside diameter of the aperture and the sidewalls. Applying such a lubricant may reduce friction and establish an improved vacuum seal between the penis and the device.

The unexpanded diameter of the aperture may vary for a range of penis diameters, so that the device properly seals around a given user's penis. Also, the urethral notch may have a greater wall thickness than the surrounding wall thickness of the sidewall. The greater wall thickness of the urethral notch may help the notch maintain its shape to prohibit constriction of the urethra as the aperture expands. The thinner surrounding wall thickness of the sidewalls relative to the urethral notch thickness may enhance the ability of a user to deform the sidewalls and webbing member when removing the device from a penis.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A unitary penile seal and constriction ring device, comprising:
    a webbing member having an outer circumference;
    a sealing ring portion of the webbing member radially spaced inwardly from the webbing member outer circumference and having a radially inwardly facing surface and a radially outwardly facing surface, in sealing contact with a second surface when in an unpressurized state; and
    an aperture formed in the webbing member, at a location radially spaced inwardly from the radially inwardly facing surface, that portion of the webbing member defining the aperture providing sealing and constricting contact with a penis.

2. The device of claim 1 further comprising channels formed in the webbing member, the channels extending generally radially outwardly.

3. The device of claim 1 wherein the device is molded from elastomeric material as a single piece.

4. The device of claim 1 wherein the sealing ring portion extends at an angle relative to a first major surface of the webbing member.

5. The device of claim 1 wherein the device is capable of being mounted to an end of a vacuum cylinder, and the second surface is an interior surface of the vacuum cylinder.

6. The device of claim 1 wherein the aperture includes sidewalls, the aperture sidewalls being configured to match anatomical features of a penis.

7. The device of claim 1 further comprising a retaining ring portion formed at the webbing member outer circumference, the retaining ring portion extending at an angle relative to a major surface of the webbing member.

8. The device of claim 7 further comprising generally radially extending channels formed in the retaining ring, wherein the channels extend outwardly from the radially outwardly facing surface of the sealing ring.

9. The device of claim 1 wherein the sealing ring portion extends at an angle relative to a first major surface of the webbing member.

10. The device of claim 1 further comprising a retaining ring portion formed at the webbing member outer circumference, the retaining ring portion extending at an angle relative to a major surface of the webbing member.

11. The device of claim 10 further comprising channels formed in the webbing member, the channels extending generally radially outwardly.

12. A penile seal and constriction ring device suited for attachment to a cylinder and to a penis, comprising:
    a webbing member having an outer circumference;
    a retaining ring portion of the webbing member formed at the webbing member outer circumference, the retaining ring portion capable of engaging an outer surface of the cylinder adjacent an end surface of the cylinder, the retaining member comprising radially extending channels;
    an sealing ring portion of the webbing member radially spaced inwardly from the outer circumference of the webbing member and having a radially outwardly facing surface, the sealing ring portion engaging an inner surface of the cylinder to form a seal with the cylinder; and
    an aperture formed in the webbing member, the aperture having sidewalls, the aperture sidewalls capable of forming a seal around the penis and constricting vessels of the penis.

13. A method of forming a seal between a penile seal and constriction ring device and a vacuum cylinder, the vacuum cylinder comprising an inner surface, an outer surface, and a first end having an end surface, the device comprising a webbing member having an outer circumference, and a sealing ring portion radially spaced inwardly from the webbing member outer circumference and having a radially outwardly facing surface, the method comprising the steps of:
    placing the device on the first end of the vacuum cylinder; and
    forming a seal between the radially outwardly facing surface of the sealing ring and the inner surface of the vacuum cylinder in an unpressurized state, the webbing member further comprising radially extending channels configured to expose that portion of the webbing that engages the outer and end surfaces of the vacuum cylinder to atmospheric pressure so as to prevent a seal from being formed between the outer and end surfaces of the vacuum cylinder and the webbing member.

14. A system for treatment of erectile dysfunction, comprising;
    a vacuum cylinder, the cylinder having an outer surface, an inner surface, and first and second ends;
    a vacuum pump removably secured to the cylinder second end, the pump capable of forming a vacuum in the cylinder; and
    a unitary penile seal and constriction ring device removably mounted to the cylinder first end, the device comprising:
        a webbing member having an outer circumference;
        a sealing ring portion of the webbing member radially spaced inwardly from the webbing member outer circumference and having a radially inwardly facing surface and a radially outwardly facing surface, extending substantially parallel to the inner surface of the vacuum cylinder to form a seal with the inner surface of the vacuum cylinder; and
        an aperture formed in the webbing member at a location radially spaced inwardly from the radially inwardly facing surface.

* * * * *